United States Patent
Wood (10) Patent No.: US 9,347,927 B2
(45) Date of Patent: May 24, 2016

(54) SYSTEMS AND METHODS FOR IMPLEMENTING ADVANCED AGENT MONITORING USING A HEATED VAPORIZER INLET APPARATUS

(71) Applicant: LOCKHEED MARTIN CORPORATION, Bethesda, MD (US)

(72) Inventor: John Wood, Bethlehem, PA (US)

(73) Assignee: Lockheed Martin Corporation, Bethesda, MD (US)

(*) Notice: Subject to any disclaimer, the term of this patent is extended or adjusted under 35 U.S.C. 154(b) by 336 days.

(21) Appl. No.: 13/918,886

(22) Filed: Jun. 14, 2013

(65) Prior Publication Data

US 2014/0366608 A1    Dec. 18, 2014

(51) Int. Cl.
*G01N 7/00*      (2006.01)
*G01N 33/00*    (2006.01)
*G01N 1/22*     (2006.01)
*G01N 1/02*     (2006.01)

(52) U.S. Cl.
CPC .......... *G01N 33/0009* (2013.01); *G01N 1/2273* (2013.01); *G01N 2001/028* (2013.01)

(58) Field of Classification Search
CPC ....... G01N 33/0009; G01N 1/44; G01N 1/28; G01N 1/42; G01N 33/0004; G01N 1/02; G01N 1/22; G01N 1/2202
USPC ................... 73/23.2, 863.11, 23.25
See application file for complete search history.

(56) References Cited

U.S. PATENT DOCUMENTS

| | | | |
|---|---|---|---|
| 3,628,310 A * | 12/1971 | Purnell | 95/86 |
| 4,269,507 A * | 5/1981 | Allen et al. | 356/36 |
| 4,433,982 A | 2/1984 | Odernheimer et al. | |
| 5,092,155 A | 3/1992 | Rounbehler et al. | |
| 6,895,804 B2 | 5/2005 | Lovell et al. | |
| 7,036,388 B1 | 5/2006 | Genovese et al. | |
| RE40,943 E * | 10/2009 | Brunsell | 210/648 |
| 7,687,276 B2 | 3/2010 | Kunz | |
| 7,749,440 B1 | 7/2010 | Genovese | |
| 8,186,234 B2 | 5/2012 | Syage et al. | |
| 2002/0007687 A1* | 1/2002 | Zimmermann et al. | 73/864.71 |
| 2003/0033851 A1 | 2/2003 | Gelfman et al. | |
| 2003/0043379 A1* | 3/2003 | Makino et al. | 356/437 |
| 2007/0039949 A1* | 2/2007 | Wilson | 219/679 |
| 2009/0282932 A1* | 11/2009 | Blackwell et al. | 73/863.21 |
| 2011/0154918 A1 | 6/2011 | Syage et al. | |

* cited by examiner

*Primary Examiner* — Eric S McCall
*Assistant Examiner* — Mohammed E Keramet-Amircolai
(74) *Attorney, Agent, or Firm* — Ronald E. Prass, Jr.; Prass LLP (57) ABSTRACT

A system and method are provided for implementing an advanced monitoring scheme to detect a localized presence of particular target substances, including toxic chemical agents, in a space, and particularly for detecting and monitoring a presence of chemical agents that are absorbed into porous or semi-porous products and surfaces in the space when it is determined that potential chemical agent exposure has occurred. A heated vaporizer inlet apparatus provides a sensor source that is optimized for the detection of less volatile chemical agents, and particular less volatile chemical agents, that have been absorbed by materials with porous compositions or surfaces. The heated vaporizer inlet apparatus is used for heating architectural surfaces that were exposed to chemical agents in an effort to substantially increase a vapor pressure of a target substance disposed on or absorbed in a particular target surface.

19 Claims, 4 Drawing Sheets

SYSTEMS AND METHODS FOR IMPLEMENTING ADVANCED AGENT MONITORING USING A HEATED VAPORIZER INLET APPARATUS

BACKGROUND

1. Field of the Disclosed Embodiments

This disclosure relates to systems and methods for implementing an advanced monitoring scheme to detect a localized presence of particular target substances, including toxic chemical agents, in a space, and particularly for detecting and monitoring a presence of chemical agents that are absorbed into porous or semi-porous products and surfaces in the space when it is determined that potential chemical agent exposure has occurred.

2. Related Art

The term "chemical agents" is generally understood by those of skill in the art to refer to a particular class of chemicals, or more specifically manufactured chemical compounds, that are produced, and may be employed, to cause various levels of debilitating physiological effects in humans. Chemical agents are engineered to produce limitedly harmful effects for crowd control, or potentially deadly effects in chemical warfare employment scenarios, by causing physiological and/or psychological reactions in the human body when applied externally, inhaled or ingested. Many chemical agents particularly cause disruption in normal bodily functions.

There are a number of different types of chemical agents. These chemical agents have a broad array of uses including targeting assemblies of people with diluted doses, or non-lethal compounds, for crowd control to concentrated dispersal of lethal compounds over an area as a chemical warfare means. Based on the danger posed by the highly toxic nature of many of the most deadly of these chemical agents, access to these particular chemical compounds is often very tightly controlled in an attempt to ensure that the highly-toxic, and potentially lethal, compounds are not accessible to unauthorized individuals for improper use.

A non-exclusive list of particularly dangerous chemical agents is catalogued in a safety pamphlet by the Department of the Army (Pamphlet No. 385-61, hereinafter "the Pamphlet") entitled "Toxic Chemical Agent Safety Standards" (revised Nov. 13, 2012). In Chapter 2, the Pamphlet broadly describes the relevant chemical agents of concern as falling into two general categories—blister agents and nerve agents. The Pamphlet goes on to describe that "[b]lister agents are persistent agents that act on the eyes, lungs, and skin and burn and blister the skin or any other part of the body they contact." This type of chemical agent is indicated to include, for example, what are commonly referred to as the "mustard" chemical agents. The Pamphlet then expands on, and defines its use of, the term nerve agents as "organophosphorus compounds chemically related to pesticides." This type of chemical agent is indicated as including what are generically, and almost innocently, referred to as the "G" and "V" agents. G agents are indicated as being generally directed at adversely affecting the human respiratory system, while V agents are indicated as producing a broad range of neurological disorders leading generally to paralysis and cardiovascular or respiratory failure. These nerve agents include, for example, GA—tabun, GB—sarin, GD—soman, and VX.

Military and law enforcement personnel receive varying levels of training with regard to (1) securing, handling and employing chemical agents (including self-protection during these evolutions), and (2) responding to all manner of release of chemical agents ranging from inadvertent releases (or spills) caused by improper handling to intentional release in crowd control scenarios or as chemical warfare attacks.

The stability and dispersal of chemical agents generally depends on environmental factors including at least temperature and humidity. These environmental effects are taken into account along with winds and precipitation potential during a deliberative planning process for employing the chemical agents as chemical weapons.

Chemical agents are not typically considered to be stored or employed in a strictly gaseous state. Rather, they are generally stored as liquids that may be handled and deployed as liquids, or that may more often be vaporized as aerosols. The typical mechanism, therefore, by which the chemical agents act is by contacting surfaces of the skin, of clothing and of structural surfaces, contaminating those surfaces even in instances where no particular immediate poisoning of a human subject occurs. Regardless of the particular storage or employment methodology, once a chemical agent has been inadvertently or purposefully released, the surfaces with which the chemical agent comes in contact are contaminated with the chemical agent often rendering the surfaces themselves toxic. Because of this, extensive monitoring is undertaken in enclosed storage facilities and significant field monitoring is appropriate when chemical agents may be deployed over an area for handling personnel or friendly force avoidance of contaminated areas.

In instances where chemical agents are detected and the areas are to be returned to common use, decontamination of facilities and/or target areas, to include widespread disposal of equipment and furnishings having contaminated surfaces, must be undertaken according to very detailed and stringent protocols to avoid harming non-intended personnel. See, e.g., Chapter 5 of the Pamphlet.

SUMMARY OF THE DISCLOSED EMBODIMENTS

Sophisticated monitoring equipment is available to detect a presence of one or more chemical agents in a particular area or on, for example, particular surfaces. Chapter 5 of the Pamphlet cautions, however, that "[i]tems or materials that are known because of air monitoring or are reasonably believed to present a chemical agent contact or vapor hazard will be managed to ensure that it is handled by the appropriate category of personnel for the level of decontamination. An item or material having been in the presence of agent vapor does not automatically mean that the item or material has been contaminated with chemical agent." Emphasis added. It is for this reason that individual items and surfaces, and even portions of surfaces, that may have been contacted by chemical agents need to be individually evaluated to determine a presence and/or a level of contamination. It is this evaluation that is central to conducting appropriate determinations regarding whether decontamination efforts can appropriately address the contamination issues or whether disposal of the contaminated devices, equipment, furniture, surfaces or the like is the only option.

The Pamphlet, at subparagraph 5-2, lays out the conditions under which tools, supplies, equipment, and facilities that may have contacted "a liquid agent or experienced a chemical agent aerosol environment" may "be considered clean and available for unrestricted use" thereby establishing a protocol that supports reclamation to the extent possible and avoids wholesale disposal. Appendix D of the Pamphlet provides a "Decontamination and disposal flow chart" that requires, among other steps, an evaluation of physical factors for the material under evaluation in support of a decision to return the material to unlimited use, with or without being subjected to decontamination.

In support of the strictures set forth in the Pamphlet, and the importance of strictly following those guidelines, and in consideration of other directives and myriad other considerations regarding handling and control of chemical agents, the U.S. Army's Chemical Biological Application and Risk Reduction (CBARR) Business Unit explore technologies that may allow for an increasingly rapid, yet precisely accurate, screening of facilities exposed to chemical agents and/or weapons to determine specific levels of contamination with regard to the individually allegedly-contaminated materials within the facilities.

Identifying specifically-contaminated materials in accordance with the guidance of the Pamphlet, and particularly as guided by the flowchart in Appendix D, can reduce the cost and time needed for decontamination by allowing only contaminated surfaces to be removed, saving the bulk of an exposed site from wholesale destruction. An ability to specifically identify a level of contamination is of particular concern with regard to comparatively non-volatile agents, such as VX, because VX has such a high toxicity and low vapor pressure. These characteristics of the VX agent make the VX agent difficult to sense rapidly when the VX agent may be present in toxicity and concentration levels of concern on, for example, architectural materials.

Conventionally, an atmospheric-pressure chemical ionization (APCI) device is provided as an ionization source used in mass spectrometry. APCI is a form of chemical ionization which takes place at atmospheric pressure providing high mass flow rates for air samples forwarded to an analyzer for spectrographic analysis. The Environmental Protection Agency (EPA) uses an APCI device as a typical input source, for example, for its Trace Atmospheric Gas Analyzer (TAGA).

TAGA is described by the EPA as a self-contained mobile laboratory capable of real-time sampling and analysis in the low parts per billion level of outdoor air or emissions from various environmental sources and concerns. TAGA, the EPA continues, has specialized sampling equipment for measuring indoor air and at remote locations. In testing by the EPA in conjunction with the Army, the APCI/TAGA combination was tested for its ability to detect vapor emitted at ambient temperature from coupons made of a variety of materials. TAGA is fielded conventionally as a most sensitive real time monitor for chemical agents such as VX. TAGA is able to detect VX vapor (normally considered non-volatile) spilled onto architectural materials at clean-up threshold levels from non-porous surfaces such as floor tile, but, despite its sophistication, may experience difficulty in detecting VX that has been absorbed into porous surfaces, including, for example, carpets or polymer door and window seals that may have been exposed to VX.

Two factors contribute to the difficulties experienced by TAGA in sensing VX on some of the more porous architectural materials. First, VX may be absorbed into the material, and the affinity of VX for the material may result in an even more reduced vapor pressure, and thus a reduced mass emission rate from the contaminated porous material. Second, the APCI source for TAGA requires high air flow rates (60 to 90 Liters/min), which substantially dilute the vapor being emitted from the room temperature porous architectural materials.

TAGA's APCI ionization source is considered to offer among the best detection limits (at levels, for example, under one part per trillion by volume (pptv)) and rapid response to changing concentrations (at intervals, for example, of under 0.5 seconds) currently available for air monitoring. That excellent capability is, however, best applied to ambient air levels, and is not well suited to detecting the presence of chemical agents on or in architectural surfaces. The high air flow needed to operate the TAGA's APCI source substantially dilutes the agent as it is being released from the architectural material. This coupled with the relative scarcity of TAGA systems, particularly as compared to the myriad available hand held detection and monitoring sensors available worldwide, leaves a gap in potential detection strategies and schemes.

In order for instruments such as the TAGA to rapidly screen for the presence of trace levels of chemical agents such as VX on architectural materials, or to expand the scope of sensors that may be used to conduct such screening, it may be beneficial to either substantially increase a rate of volatilization of a particular chemical agent for detection or to significantly decrease a flow rate of air in which chemical components of the particular chemical agent may be entrained being pulled over the contaminated surface and into the detector. A combination of increasing volatilization and decreasing air flow may enable monitors less sensitive than the TAGA to successfully screen the selected architectural materials at the required contamination levels.

In view of the above observations, it would be advantageous to provide a system and a method for addressing the difficulties enumerated above by providing a sensor source that is optimized for the detection of less volatile chemical agents, and particular less volatile chemical agents, that have been absorbed by materials with porous compositions or surfaces.

Exemplary embodiments of the systems and methods according to this disclosure may provide a heated vaporizer/inlet (HVI) apparatus for heating architectural surfaces that may have been exposed to chemical agents in an effort to substantially increase a vapor pressure of a target substance disposed on or absorbed in a particular target surface.

Exemplary embodiments may provide a heated, controlled-rate airflow for heating the potentially chemically exposed surface to a temperature higher than ambient, and optimally to approximately 120° C. The heated airflow mechanism may heat the exposed area to potentially increase a concentration of the target substance entrained in the controlled-rate (low pressure/rate) airstream that is passed to an air quality analyzer or monitor. Heating the potentially exposed surface to 120° C. can be expected to increase the vapor pressure, for example, by about a factor of 100 times or more.

Exemplary embodiments may use a lower air flow rate over, or penetratingly into, an architectural surface, and particularly a porous architectural surface, that is suspected of having been contaminated. A concentration of a chemical agent contaminant that is caused to be emitted into the air flow by the heating at a constant mass emission rate may substantially increase and make more detectable a concentration of the target chemical agent substance in the air passing over or through the surface.

Exemplary embodiments may make particularly advantageous use of the combination of the above effects to provide a more highly concentrated air mass in which the chemical agent is entrained to allow for classes of less sensitive (and correspondingly less expensive), and more readily available, detectors, monitors, analyzers, sensors or the like to be used in a manner that may be comparable to the performance of the TAGA's APCI source for detecting a presence of less volatile chemical agents on or in architectural surfaces.

Exemplary embodiments of the disclosed HVI may incorporate a particularly configured structure and integrate simple components in a manner that is particularly suited to accommodating much lower air flows, making it possible for much less sensitive monitors to be able to detect relatively non-volatile chemical agents at the required surface concentration detection levels.

Exemplary embodiments of the disclosed HVI-centric schemes may substantially improve an ability, and a range, of instrumentation to detect trace levels of target chemical agent substances on or in architectural materials, thereby affording users an increased capacity to rapidly determine which materials are contaminated, and to what relative levels of contamination, in support of determinations as to whether the materials can be decontaminated to safe exposure levels or disposal is an only viable option for making a particular area safe. This capacity affords the users an opportunity to avoid complete destruction of contaminated facilities based on an increased ability to identify specifically-contaminated areas, equipment, surfaces and the like.

These and other features, and advantages, of the disclosed systems and methods are described in, or apparent from, the following detailed description of various exemplary embodiments.

BRIEF DESCRIPTION OF THE DRAWINGS

Various exemplary embodiments of the systems and methods for implementing an advanced monitoring scheme to detect a localized presence of chemical agents in a space, and particularly for detecting and monitoring a presence of chemical agents that are absorbed into porous or semi-porous products and surfaces in the space when it is determined that potential chemical agent exposure has occurred, will be described, in detail, with reference to the following drawings, in which.

DETAILED DESCRIPTION OF THE DISCLOSED EMBODIMENTS

The disclosed systems and methods for implementing an advanced monitoring scheme to detect a localized presence of chemical agents in a space, and particularly for detecting and monitoring a presence of chemical agents that are absorbed into porous or semi-porous products and surfaces in the space when it is determined that potential chemical agent exposure has occurred, will generally refer to this specific utility for those systems and methods. Exemplary embodiments described and depicted in this disclosure should not be interpreted as being specifically limited to implementation in any particular architectural space, or in examination of any particular non-porous or porous material or surface within a space, or as being directed at any particular chemical agent, or as being targeted to only chemical agents. In fact, any advantageous use of a controlled-rate of a heated airflow across and/or into a contaminated surface that may aid in releasing lower volatility chemical compounds, particularly from porous surfaces, for ease of detection by downstream sensors to which the airflow is exposed is contemplated.

Specific reference to, for example, any particular chemical agent or any particular airborne contaminant detector, analyzer or sensor, or any analyzing scheme, should be understood as being exemplary only, and not limiting, in any manner, to any particular chemical agent for detection or any particular class of devices for conducting airborne contaminant sensing, detection, analysis and the like. The systems and methods according to this disclosure will be described as being particularly adaptable to appropriately conditioning low volatility chemical agent compounds disposed on or absorbed in materials for presentation to an analyzer to assess levels of contamination in support of determinations as to whether the materials can be decontaminated or need to be disposed of in order to cleanse a particular space that was exposed to contamination. The disclosed systems and methods should not be considered as limited to only those particular or specified functions.

Further, although described as being particularly directed to detection of toxic chemical agents, the disclosed systems and methods may be directed at the detection of many less toxic low volatility compounds. In this regard, the term "contamination," and the related concepts, as used in this disclosure, are intended to be expansive and broadly inclusive rather than exclusive to, for example, toxic chemical agents.

Individual features and advantages of the disclosed systems and methods will be set forth in the description that follows, and will be, in part, obvious from the description, or may be learned by practice of the features described in this disclosure. The features and advantages of the systems and methods according to this disclosure may be realized and obtained by means of the individual elements and combinations of those elements as particularly pointed out in the appended claims. While specific implementations are discussed, it should be understood that this is done for illustration purposes only. A person skilled in the relevant art will recognize that other components and configurations may be used without departing from the spirit and scope of the subject matter of this disclosure.

Various aspects of the disclosed embodiments relate to a system and a method for implementing heated vaporization of a target substance in support of an advanced chemical agent monitoring scheme. The disclosed concepts for a heated vaporizer/inlet (HVI) generally include a particularly-configured apparatus for passing a controlled flow of heated air over or into an architectural surface, a furniture surface or an equipment component surface. The controlled flow of heated air elevates a temperature of the target surface, preferably in a range of about 120° C. The elevated temperature causes the vapor pressure of a target substance in or on the target surface to increase substantially. The elevation of the vapor pressure of the target substance under heating of the target surface causes a coincident substantial increase in a concentration of the target substance to be entrained in an airstream of the controlled flow of heated air passed over or into the target surface. The airstream is directed toward a detecting, monitoring, sensing or analyzing apparatus. Heating the surface to 120° C. may be expected to increase the vapor pressure by about a factor of approximately 100 times or more.

Using a lower air flow rate over or into a contaminated target surface when the target substance (contaminant) is being emitted at a constant mass emission rate substantially increases the concentration of the target substance in the air passing over or through the target surface. Therefore, a less sensitive detector can be used for detecting the target substance pulled from on or in the target surface when the less sensitive detector is configured to use a substantially lower air flow. The disclosed HVI may be designed to accommodate much lower air flows, making it possible for such less sensitive monitors to be able to detect comparatively less volatile chemical agents as target substances at the required surface concentration detection levels. For example, while the EPA's TAGA cane use a low pressure chemical ionization (LPCI) source is 10 to 100 times less sensitive than the APCI source for these classes of compounds, it draws only 10 milliliters per minute (mL/min) into the instrument, as opposed to around 90,000 mL/min used for the APCI. At the same mass emission rate from the architectural materials, the concentration of the target substance in the air stream reaching the LPCI can be expected to be well over 1000 times higher, potentially making the LPCI the more suitable choice for this application.

Existing monitors, other than the EPA's TAGA, may specifically benefit from using the HVI, so the HVI would be a good addition to any real time chemical agent or other target substance monitor when screening for surface contaminants. With the addition of the HVI, hand-held monitors designed for action level ambient air monitoring may be converted into monitors suitable for identification of contaminated architectural surfaces.

The disclosed HVI apparatus or scheme may substantially improve the ability of instrumentation to detect trace levels of target substances on or in target surfaces including architectural materials, thereby offering users an ability to rapidly determine which materials are contaminated and need to be removed, and which materials may simply be decontaminated. The disclosed concepts offer users an ability, for example, to avoid complete destruction of contaminated facilities because the contaminated areas on equipment, furniture and/or structures and surfaces can be more easily identified and localized for excision.

Figure 1:
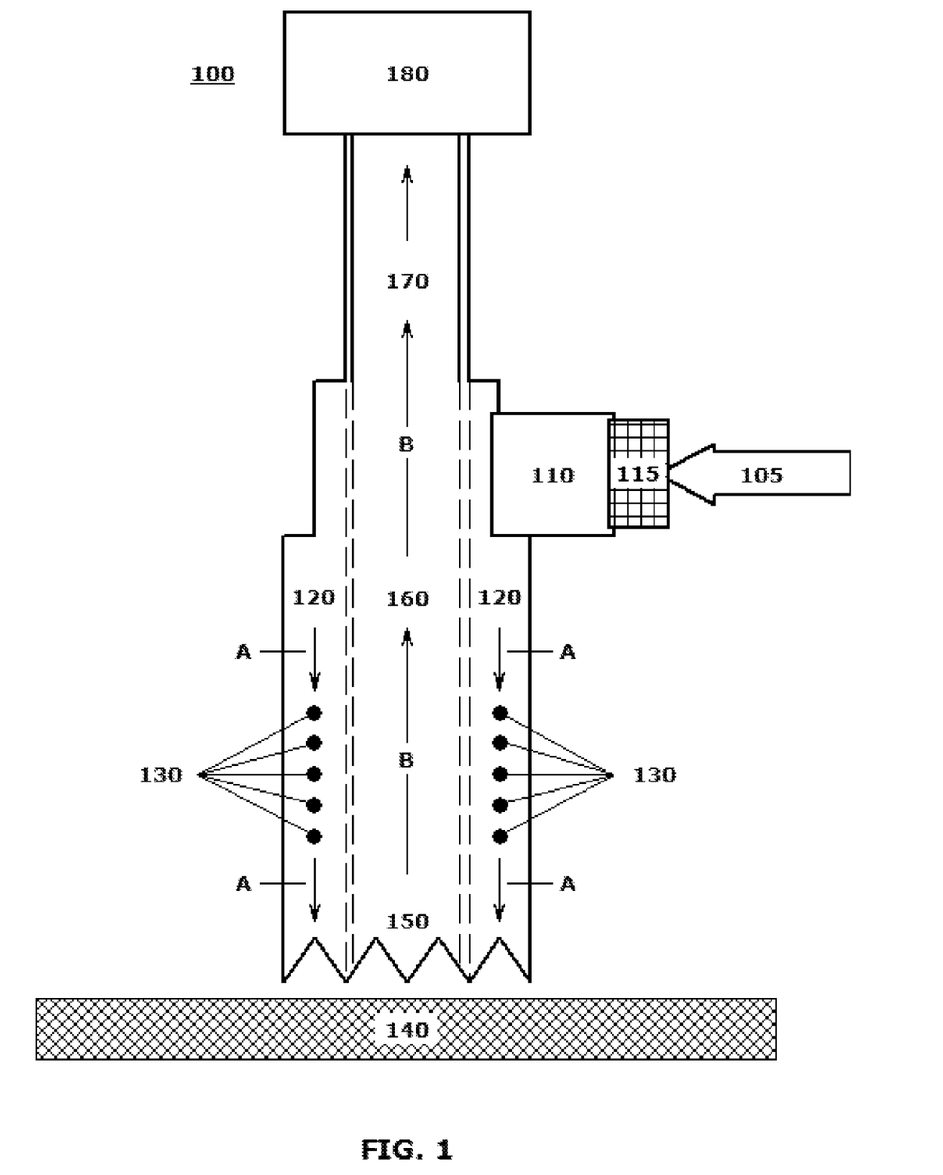
FIG. 1 illustrates a first exemplary embodiment of a heated vaporizer inlet (HVI) assembly for supporting chemical agent detection and monitoring according to this disclosure.

FIG. 1 illustrates a first exemplary embodiment of a heated vaporizer inlet (HVI) assembly 100 for supporting chemical agent detection and monitoring by an analyzer 180 according to this disclosure. As shown in FIG. 1, the exemplary HVI assembly 100 may provide a forced flow of heated air in a direction "A" toward a target surface 140 to release target substances that are disposed on the target surface 140 or potentially that are absorbed in the target surface 140. This action may raise a volatility of the target substances in a manner that causes elements of the target substances to be released from the target surface 140 and entrained in the heated, and potentially penetrating, air stream prior to its redirection toward the analyzer 180. The exemplary HVI assembly 100 may provide a separate recovery airflow pathway for sucking air, at a slightly higher rate, in a direction "B" away from the target surface 140 and toward an inlet of the air analyzer 180 for analysis of substances released from the target surface and entrained in the recovery air stream. In this manner, an analysis of the recovered air may provide the user a basis for a determination regarding whether all, or a portion of, the target surface 140 is contaminated and to what extent.

A first portion of the exemplary HVI assembly 100 may consist of a radially segregated body portion that includes an outer annular air supply chamber 120 and an inner bore air recovery chamber 160. A flow of external ambient air 105 from within the space may be drawn into the exemplary HVI assembly 100 by a blower component 110, optionally through a filter component 115. It should be recognized that, in a contaminated space, the ambient air within the space may be contaminated to some level with the very target substances that are sought to be detected on or from the target surface 140. In order to provide more accuracy in an evaluation of the contamination levels of the target surface 140, it may be appropriate, or even necessary, to filter the incoming air drawn in by the blower component 110 in a manner that removes contaminants entrained in the ambient air. The filtration, via a filter component 115 or the like, should also occur upstream of any heating elements (see elements 130, as described below) in order that the filtration effects of the selected filtering substance are not adversely affected. In this regard, positioning the filter component 115, as shown, at an inlet area of the blower component 110, or otherwise at an outlet area of an unheated blower component, upstream of any heater elements 130 may be useful to aid in ensuring that the external air 105, which may be contaminated with the target substance, is appropriately filtered in a manner that may not adversely affect the analysis of the contamination level of the target surface 140.

In addition to filtering the ambient air entering the blower component 110, and/or filtering the ambient air upstream of the heater elements 130, which is appropriate to cleanse the provide a 'clean' background, it may also be desirable to provide a heated particulate filter in the airstream in the inner bore air recovery chamber 160 leading from the target surface 140 to an inlet of the analyzer 140. This heated particulate filter may be a particulate filter that may be raised to a temperature somewhat higher than the vaporization temperature of the air impinging onto and into the target surface 140. Differing from the filter component 115 that may be comprised of a combination chemical/particulate filter to remove both particulate and chemical vapor contamination, the heated particulate filter may be designed and operated in a manner that removes particulate contamination from the airstream being presented to the analyzer 180 while allowing the elements of the vapor contamination released from the target surface 140 to pass to the analyzer 180.

In embodiments, a separate and segregated air supply source (not shown) may be provided. The separate air supply source may be, for example, an inert gas supply source that may be provided to offset, for example, potential high temperature oxidation issues with regard to the components of the target substances that may be entrained in the recovery airflow path once released from the target surface 140, as described below.

Forced air expelled from the blower component 110, filtered or not, may be directed by the outer annular air supply chamber 120 in direction "A" toward an open end 150 of the exemplary HVI assembly 100. The force of the airflow impinging on, and potentially penetrating, the target surface 140 may be particularly helpful in forcing the release of, or otherwise driving, elevated volatility components of the target substances from semi-porous or porous surfaces and/or compositions of the of the target surface 140. A principal reason for using jets of heated air in the exemplary HVI 100 is to provide a mechanism by which the heated air may penetrate into a porous target surface 140, thereby heating and vaporizing material from below the nominal surface or top face of the target surface 140 and carrying the vaporized material out of the porous surface, e.g., carpet and into the air stream being drawn into the inner bore air recovery chamber 160

In the embodiment shown in FIG. 1, heater elements 130 may be placed in the outer annular air supply chamber 120 to elevate the temperature of the forced flow of supply air. The heater elements 130 may be annular or ring shaped, substantially comporting with a configuration of the outer annular air supply chamber 120, but may be of other shapes, compositions or configurations and disposed appropriately in the outer annular air supply chamber 120 as well.

The heater elements 130 may be controlled in a manner that elevates the temperature of the supply air flow to a temperature high enough to substantially raise the vapor pressure of the target substance while not high enough to (1) cause undesired chemical changes/reactions (such as oxidation) in a composition of the target substance, or (2) cause damage to the target surface 140 through heated air impact on the target surface 140, or inadvertent contact of the distal end of the exemplary HVI assembly 100 with the target surface 140. This control, as will be described in greater detail below, may be based on reference to a stored set of material characteristics for typical target substances and typical materials from which the target surface 140 may be formed or manufactured. The material characteristics may include, for example, vaporization temperature ranges for a plurality of target substances, physical/chemical property changing temperature ranges for the plurality of target substances and/or destructive temperature limits/ranges for the plurality of target substances and the myriad materials from which the target surface 140 may be formed.

Heated supply air may exit an open end 150 of the exemplary HVI assembly 100 with a force sufficient to vaporize target substances disposed on, or absorbed in, the target surface 140. This action raises the vapor pressure of the target substances and causes components of the target substances to be entrained in the recovery airstream drawn in direction "B" into and through the inner bore air recovery chamber 160. A rate of flow of the heated supply air toward impingement onto or into the target surface 140 may be controlled, even for a constant pressure blower component 110, by controlling a size of orifices at the open end 150 using known methods. These known methods may include providing interchangeable end caps with differing numbers and/or sizes of exit orifices, or by providing adjustable valve or orifice members, including, for example, iris-type valves associated with the exit orifices, or by using other like techniques.

The open end 150 may be configured in a manner that attempts to ensure that the jets of heated air originate close to the target surface 140, while spaces are provided at a periphery of the open end 150 to provide conduits via which outside air at the target surface may be drawn into the inner bore air recovery chamber 160 in a manner that limits the production of a local vacuum. As shown in FIG. 1, a scalloped edge design for the open end 150 may provide such a configuration. In operation, a careless operator might raise the open end 150 too high above the target surface to be effective, or may tilt the HVI 100 with respect to the target surface 140 such that the open end 150 is substantially away from vertical, thus creating a false sense of security regarding contamination. An appropriate configuration of the open end 150 that allows for partial contact with the target surface to reduce deviations in effectiveness that may be introduced through improper placement of the device. In embodiments, a sensor system may be advantageously included to provide an indicator for vertical placement of the device and within a particular proximity to a target surface 140 for maximum effectiveness. The sensor may be a simple mechanical apparatus such as an easily cleaned wire loop, or may be as complex as an ultrasonic distance sensor, with a light indicating that an operator has positioned the device correctly and within an acceptable range of the target surface.

A second portion of the exemplary HVI assembly 100 may consist of an insulated air guide 170 that may be positioned essentially as an extension of the inner bore air recovery chamber 160. Although shown in FIG. 1 as being aligned in a straight path from, and coaxial with, the inner bore air recovery chamber 160, the insulated air guide 170 may be configured as appropriate to provide an interface between the first portion of the exemplary HVI assembly 100 and the input to the analyzer 180, or between the first portion of the exemplary HVI assembly 100 and some intermediate component that may be used to, for example, precondition the recovery air stream for introduction to a sensor input of the analyzer 180.

The exemplary HVI assembly 100 may be formed of a smooth non-porous material, e.g., stainless steel, that may pass the plurality of air streams generally in the directions shown without constriction and avoiding unnecessary deposition of entrained components, for example, on an inner surface of either the inner bore air recovery chamber 160 or the insulated air guide 170. Outer surfaces of the exemplary HVI assembly 100 should comprise, at least in part, non-heat conducting handling portions (not shown) to avoid injury to users from contacting heated components that may be heated to temperatures of 120° C. and above. Particular selection may be appropriate for a material from which the open end 150 structure(s) may be formed. An appropriate material may be, for example, a non-heat conducting composite such as, for example, MACOR®, which is a machinable glass ceramic composite product manufactured by Corning Inc.® MACOR®, for example, is a non-porous substance that has excellent physical properties, high dielectric strength, electrical resistivity, high temperature tolerance and resistance, and low thermal conductivity. Its machinability makes it capable of being machined into appropriate shapes for the open end 150. These properties of the substance, or of any material from which the open end 150 may be formed, make it preferable, for instance, in fashioning the open end 150 of the exemplary HVI assembly 100 to prevent the excessive heating of the tip of the assembly in use. Inadvertent local damage to the target surface 140 may be avoided even when the target surface 140 is accidentally touched by the open end 150 of the exemplary HVI assembly 100.

Figure 2:
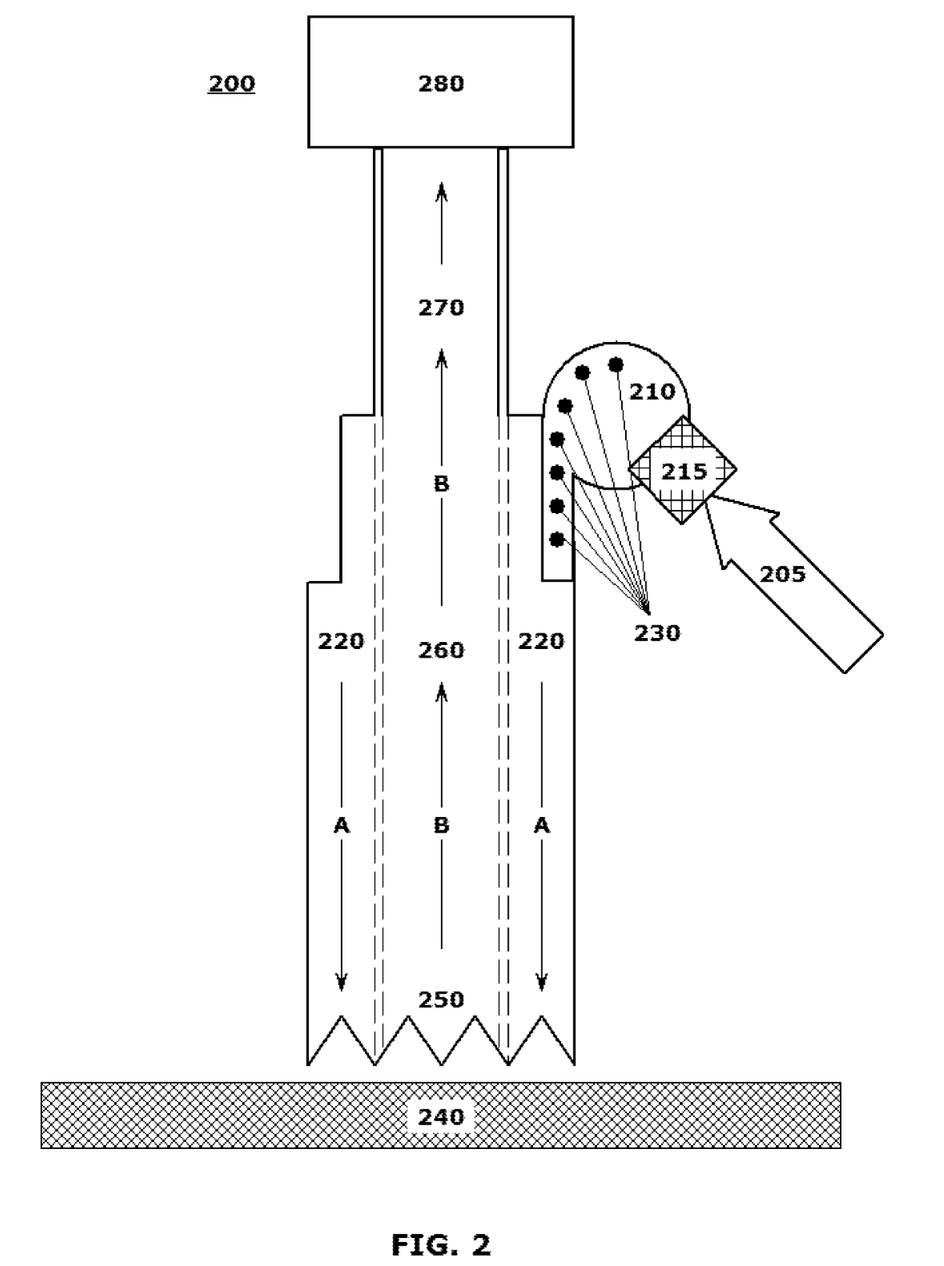
FIG. 2 illustrates a second exemplary embodiment of an HVI assembly for supporting chemical agent detection and monitoring according to this disclosure.

FIG. 2 illustrates a second exemplary embodiment of an HVI assembly 200 for supporting chemical agent detection and monitoring by an analyzer 280 according to this disclosure. Many of the component elements of the second exemplary HVI assembly 200, as shown in FIG. 2, correspond to the component elements of the exemplary HVI assembly 100, shown in FIG. 1. These include, as generally depicted, the flow of supply air in direction "A" through the outer annular air supply chamber 220, out through an appropriately configured open end 250 toward a target surface 240 to release target substances that are disposed on, or absorbed in, the target surface 240 in the manner described above. In like manner to the first exemplary embodiment of FIG. 1, the exemplary HVI assembly 200 may provide a separate recovery airflow pathway through an inner bore air recovery chamber 260 and an insulated air guide 270 for sucking air at a slightly higher rate in a direction "B" away from the target surface 240 and toward an inlet of the air analyzer 280 for analysis of substances released from the target surface 240 and entrained in the recovery air stream.

A principal difference from the embodiment shown in FIG. 1, is that the first portion of the exemplary HVI assembly 200 may draw a supply of external ambient air 205 from within the space into the exemplary HVI assembly 200 via a heated blower component 210, optionally through a filter component 215 (as above).

In the embodiment shown in FIG. 2, heater elements 230 may be placed within, or may be included as components of, the heated blower component 210. Here, control of the heated blower component 210 may include separate or coincident control of the heater elements 230, appropriately configured to be placed in the heated blower component 210, or in an outlet portion thereof, in a manner that elevates the temperature of the supply air flow exiting the heated blower component 210 to a temperature high enough to cause the advantageous physical reactions described in detail above, while avoiding the detrimental physical interactions including damage from inadvertent overheating of the target surface 240 or the target substances. Other operations and functions of the embodiment shown in FIG. 2 correspond generally to the detailed description of the operations and functions of the embodiment shown in FIG. 1, as described in detail above.

Forced air heated flow emanating from an exemplary structure such as that shown in either of FIGS. 1 and 2, has the advantage of heating the material of the target surface 140, 240 in a penetrable manner thereby more effectively releasing components of the target substances to be entrained in the return airflow. Maintaining vacuum in the return air supply in which a rate of flow of the recovery air flow is greater than a rate of flow of the air supply has the advantage of allowing for the heated penetrating airflow to impact the target surface 140,240 without being dispersed within the space. Near complete recovery of contaminated return air can be substantially assured based on the flow rate differential, thereby enhancing safety for site personnel employing the instruments and associated analyzers to assess local contamination levels. Maintaining a constant flow of the air supply while differentially adjusting an orifice size of the openings in the distal end of the outer annular supply chamber 120,220 may allow for directed penetration of the target surface 140,240 based on an evaluation of the material of which the target surface 140,240 is formed.

The above two exemplary embodiments are depicted in detail as examples of a structure of an HVI according to this disclosure for context and ease of understanding of the disclosed concepts. Those of skill in the art will recognize that many different configurations of the disclosed structures are available including that the supply air and return air paths may be reversed such that supply air is properly provided down an inner core from a corresponding air supply source, heater elements are appropriately placed in the supply stream and recovery of a return air stream may occur via a radially outer annular chamber that includes a fluid flow interface for properly directing the return air to an analyzer. A configuration that includes a plurality of parallel tubes for supply and recovery of the airstreams may be employed as well. In other words, no particularly limiting configuration to the HVI assembly structure should be inferred from the depictions in FIGS. 1 and 2.

Figure 3:
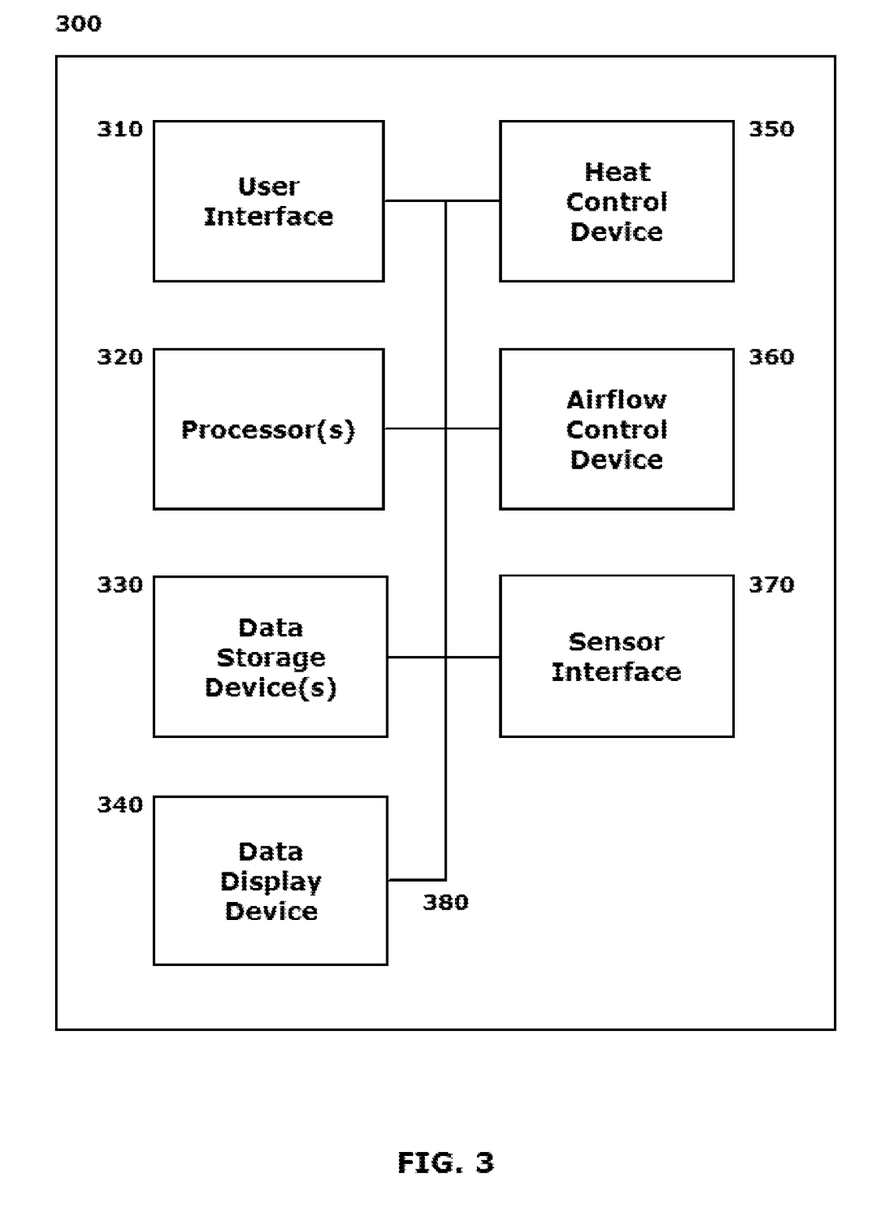
FIG. 3 illustrates a block diagram of an exemplary control system for implementing heated vaporization of target substances using an HVI in support of an advanced chemical agent monitoring scheme according to this disclosure.

FIG. 3 illustrates a block diagram of an exemplary control system 300 for implementing heated vaporization in support of an advanced chemical agent monitoring scheme according to this disclosure. The exemplary control system shown in FIG. 1 may be individually associated with one or more HVI assemblies. The one or more controlled HVI assemblies may be employed, for example, as part(s) of an overall system that may include a capacity by which to measure the distance and direction from a predetermined reference point, potentially a 'start point,' so as to be able to produce a graphic showing of the contaminated area, and even with potentially iso-concentration lines like topographic maps, with position and concentration data for each measured point.

The exemplary control system 300 may include a user interface 310 by which the user may communicate with the exemplary control system 300. The user interface 310 may be configured as one or more conventional mechanisms that permit a user to input information to the exemplary control system 300. The user interface 310 may include, for example, a keyboard or a touchscreen with "soft" buttons, or other like device for user operation of, and data exchange with, the exemplary control system 300. The user interface 310 may be used, for example, to turn ON or OFF, or to otherwise adjust operation of blower or heater components in an HVI assembly via the exemplary control system 300.

The exemplary control system 300 may include one or more processor(s) 320 for individually operating the exemplary control system 300, for making adjustments in HVI operations according to feedback received, for example, from an air analyzer serviced by the HVI and for carrying out any other processing and control functions with respect to the HVI assemble, and the target substance detection and monitoring functions. Processor(s) 320 may include at least one conventional processor or microprocessor that interprets and executes instructions to carry into effect the control functions in support of target substance detection and monitoring, particularly using a disclosed HVI assembly, according to the methods of this disclosure.

The exemplary control system 300 may include one or more data storage device(s) 330. Such data storage device(s) 330 may be used to store data or operating programs to be used by the exemplary control system 300, and specifically the processor(s) 320. Data storage device(s) 330 may include a random access memory (RAM) or another type of dynamic storage device that stores information and instructions for execution by processor(s) 320. Data storage device(s) 330 may also include a read-only memory (ROM), which may include a conventional ROM device or another type of static storage device that stores static information and instructions for processor(s) 320. Further, the data storage device(s) 330 may be integral to the exemplary control system 300, or may be provided external to, and in wired or wireless communication with, the exemplary control system 300.

One or more of the data storage devices 330 may be configured to store a database of material characteristics for typical target substances and typical materials from which target surfaces to be examined may be formed or manufactured. The material characteristics may include, for example, vaporization temperature ranges for a plurality of target substances, physical/chemical property changing temperature ranges for the plurality of target substances and destructive temperature limits/ranges for the plurality of target substances and the myriad materials from which the target surfaces may be formed. Reference may be made to these characteristics to determine an appropriate temperature range to set heating elements in an HVI in order that target substance detection may be maximized, or optimized, while any threat of damage to, or destruction of, target surfaces due to overheating may be minimized or effectively eliminated.

The exemplary control system 300 may include at least one data display device 340 which may be configured as one or more conventional mechanisms that output information to a user, including a display for alerting a user as to operating conditions of an HVI assembly or to a detected presence of a target substance, such as a chemical agent, based on feedback from an analyzer that is serviced by the HVI assembly. The data display device 340 may, with the user interface 310, constitute a portion of a graphical user interface (GUI) associated with the HVI assembly, for control of the HVI assembly. The data display device 340 may separately or additionally consist of an output port for connection to a printer, a copier, a scanner, a multi-function device, or a remote storage medium, such as a memory in the form, for example, of a magnetic or optical disk with a corresponding disk drive in order to record information on contamination of target surfaces for later review and mapping.

The exemplary control system 300 may also include a heat control device 350 and an airflow control device 360, which may operate as a part or a function of a processor 320, in conjunction with a processor 320 and/or a data storage device 330, or as separate component modules or circuits in the exemplary control system 300. The heat control device 350 and the airflow control device 360 may include at least a mechanism for enabling precise control of the blower component, the heater elements and potentially the exit orifices in operation of the HVI assembly and support of the detection and monitoring functions.

The exemplary control system 300 may include one or more sensor interface(s) 370 by which the exemplary control system 300 may communicate with components external to the exemplary control system 300 to receive feedback from an analyzer, detector, sensor, monitor or the like that is supported by the HVI assembly associated with the exemplary control system 300. Sensor interface(s) 370 may include any mechanism that facilitates communication with the analyzer, detector, sensor or monitor. As such, sensor interface(s) 370 may be appropriately configured and include such other mechanisms as may be appropriate for assisting in communications with other devices and/or systems.

All of the various components of the exemplary control system 300, as depicted in FIG. 3, may be connected by one or more data/control busses 380. These data/control busses 380 may provide wired or wireless communication between the various components of the exemplary control system 300, whether all of those components are housed integrally as a single system, or are otherwise external to and in wired or wireless communication with the exemplary system 300.

It should be appreciated that, although depicted in FIG. 3 as an integral unit, the various disclosed elements of the exemplary control system 300 may be arranged in any combination of sub-systems as individual components or combinations of components, integral to a single unit, or external to, and in wired or wireless communication with the single unit of the exemplary control system 300. In other words, no specific configuration as an integral unit, or as a support unit, is to be implied by the depiction in FIG. 3.

It should also be appreciated that the system storage and processing functions described above, given the proper inputs, may be carried out in system hardware circuits, software modules or instructions or firmware, or in varying combinations of these.

Figure 4:
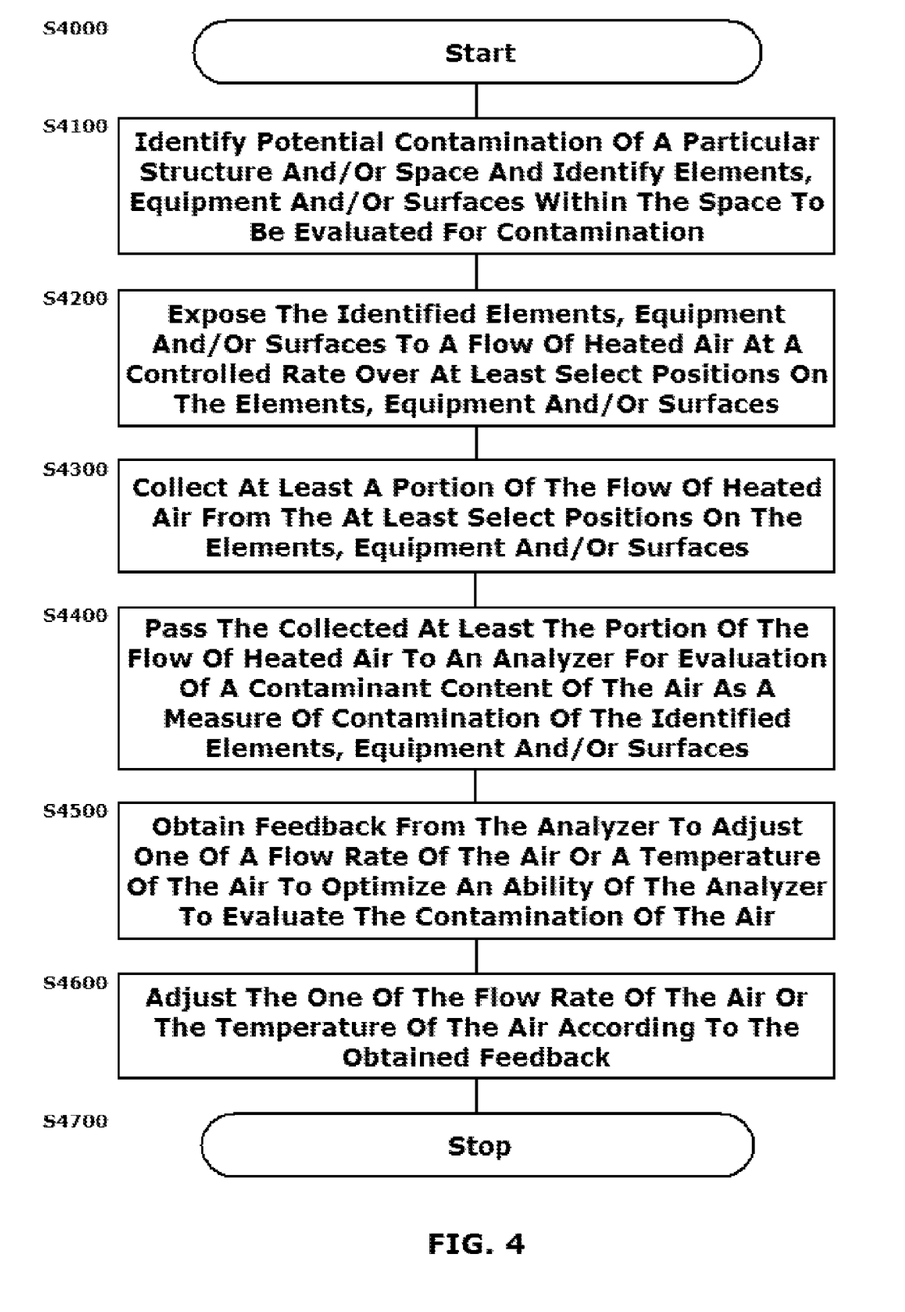
FIG. 4 illustrates a flowchart of an exemplary method for implementing heated vaporization using an HVI in support of an advanced chemical agent monitoring scheme according to this disclosure.

The disclosed embodiments may include a method for implementing heated vaporization in support of an advanced chemical agent monitoring scheme. FIG. 4 illustrates a flowchart of such an exemplary method. As shown in FIG. 4, operation of the method commences at Step S4000 and proceeds to Step S4100.

In Step S4100, potential contamination of a particular structure and/or space may be determined specifically to identify elements, equipment and/or surfaces within the space to be evaluated for contamination. Operation of the method proceeds to Step S4200.

In Step S4200, at least select positions on surfaces of the identified elements or equipment, and/or individual architectural surfaces, may be exposed to a flow of heated air at a controlled flow rate. Operation of the method proceeds to Step S4300.

In Step S4300, at least a portion of the flow of heated air from the select positions on the elements, equipment and/or surfaces may be collected by a collection element. The collection of the flow of heated air may preferably be at a rate that is higher than the supply rate in order to avoid dispersing released components of target substances. Operation of the method proceeds to Step S4400.

In Step S4400, the collected flow of heated air may be passed to an analyzer for evaluation of a contaminant content of the air as a measure of contamination of the identified elements, equipment and/or surfaces. Operation of the proceeds to Step S4500.

In Step S4500, feedback from the analyzer may be obtained to adjust one of a flow rate of the air or a temperature of the air to optimize an ability of the analyzer to evaluate the contamination of the air. Operation of the method proceeds to Step S4600.

In Step S4600, at least one of the flow rate of the air or the temperature of the air may be adjusted according to the obtained feedback. Operation of the method proceeds to Step S4700, where operation of the method ceases.

The disclosed embodiments may include a non-transitory computer-readable medium storing instructions which, when executed by a processor, may cause the processor to execute the steps of an exemplary method as outlined above.

The above-described exemplary system and method reference certain conventional components and known air analysis processes and protocols to provide a brief, general description of a suitable scheme in which the subject matter of this disclosure may be implemented for familiarity and ease of understanding. As indicated above, although not required, embodiments of the control functions according to the disclosure may be provided, at least in part, in a form of hardware circuits, firmware or software computer-executable instructions to carry out the specific functions described, such as program modules, being executed by a processor. Generally, program modules include routine programs, objects, components, data structures, and the like that perform particular tasks or implement particular data types.

Those skilled in the art will appreciate that other embodiments of the disclosed subject matter may be practiced with many types and configurations of detection and monitoring equipment and supporting structures.

The exemplary depicted sequence of executable instructions or associated data structures represents one example of a corresponding sequence of acts for implementing the functions described in the steps. No specific order is to be implied by the depiction presented in FIG. 4 and the accompanying description except where a specific method step may be considered a necessary precondition to execution of any other method step.

Although the above description may contain specific details, they should not be construed as limiting the claims in any way. Other configurations of the described embodiments of the disclosed systems and methods are part of the scope of this disclosure. For example, the principles of the disclosure may be applied to each individual user where each user may individually deploy with an HVI assembly. This enables each user to use the benefits of the disclosure. There may be multiple instances of the components each processing the air content emanating from a target surface in a variety of possible ways. It does not necessarily need to be one identical embodiment of the disclosed system used by all end users. Accordingly, the appended claims and their legal equivalents should only define the disclosure, rather than any specific examples given.

I claim:

1. A method for providing an air sample associated with a contamination level of a target surface to an analyzer, comprising:
   directing a stream of air along a first air flow path in a device between an air supply source and an exit opening at an end of the device;
   controlling, with a processor, a flow rate of the stream of air by controlling a pressure of air from the air supply source;
   heating the stream of air upstream of the exit opening at the end of the device;
   directing the stream of heated air from the exit opening toward a target surface, an impingement of the stream of heated air on the target surface causing a release of a target substance by raising a vapor pressure of the target substance, at least a portion of the target substance being entrained in the stream of heated air;
   collecting a volume of return air via a second air flow path in the device, the volume of return air being at least a portion of the stream of heated air with the at least the portion of the target substance entrained therein, the second air flow path being a separate and distinct air flow path from the first air flow path;
   directing the return air via the second air flow path to an air analyzer for analysis of the target substance as an indication of a contamination level of the target surface;
   receiving feedback, with the processor, from the air analyzer regarding a volume of entrained components from the target substance detected in the return air; and
   adjusting, with the processor, a flow rate and a temperature of the stream of heated air based on the feedback.

2. The method of claim 1, further comprising supplying the air for the stream of air directed along the first air flow path with the air supply source, the air supply source being a blower unit that takes in ambient air through an inlet and exhausts the air for the stream of air directed along the first flow path from an outlet,
   the processor controlling the pressure of the air exhausted from the blower unit via the outlet.

3. The method of claim 2, further comprising filtering the air through a filter element placed at least one of in the inlet or in the outlet of the blower unit.

4. The method of claim 2, the heating the stream of air comprising passing the air over heater elements, the heater elements being located at least one of (1) within the blower unit, or (2) in the first air flow path between the blower unit and exit opening.

5. The method of claim 4, further comprising controlling, with the processor, a temperature of the heater elements to produce a selected temperature for the stream of heated air exiting the exit opening of the first air flow path.

6. The method of claim 5, further comprising controlling, with the processor, a flow rate of the return air in the second air flow path to be greater than a flow rate of the stream of air in the first flow path.

7. The method of claim 5, further comprising:
   storing a database of material characteristics for at least one of a plurality of user-selectable target substances or at least one of a plurality of user-selectable surface materials from which the target surface may be formed.

8. The method of claim 7, the material characteristics including at least one of vaporization temperature ranges for the plurality of target substances, physical property changing temperature ranges for the plurality of target substances, chemical property changing temperature ranges for the plurality of target substances or destructive temperature limits ranges for the plurality of target substances or the plurality of surface materials.

9. The method of claim 8, further comprising:
   receiving, via a user interface with the processor, a user input regarding a user-selected at least one of the target substance or the surface material from which the target surface is formed;
   referencing, with the processor, the stored database of material characteristics; and
   initially adjusting, with the processor, at least one of the flow rate or the temperature of the stream of heated air based on the received user input regarding the at least one of the target substance or the surface material from which the target surface is formed.

10. A system for providing an air sample associated with a contamination level of a target surface to an analyzer, comprising:
    a controllable air supply source;
    a first air flow path that directs a stream of air along between the air supply source and an exit opening;
    at least one heater element that heats the stream of air in the first airflow path upstream of the exit opening, the exit opening being configured to selectively direct the stream of heated air exiting the exit opening toward a target surface, an impingement of the stream of heated air on the target surface causing a release of a target substance by raising a vapor pressure of the target substance, at least a portion of the target substance being entrained in the stream of heated air;
    a second air flow path that collects a volume of return air from the target surface, the volume of return air being at least a portion of the stream of heated air with the at least the portion of the target substance entrained therein, the second air flow path being a separate and distinct air flow path from the first air flow path;
    a conduit that directs the return air from the second air flow path to an input of an air analyzer for analysis of the target substance entrained in the return air as an indication of a contamination level of the target surface; and
    a processor that is configured to
       control a flow rate of the stream of air by controlling a pressure of air from the air supply source;
       receive feedback from the air analyzer regarding a volume of entrained components from the target substance detected in the return air; and
       adjust a flow rate and a temperature of the heated stream of air based on the feedback.

11. The system of claim 10, the air supply source comprising a separate and self-contained gas source that supplies an inert gas to the first air flow path.

12. The system of claim 10, the air supply source comprising a blower unit that takes in ambient air through an inlet and exhausts the air for the stream of air directed along the first flow path from an outlet.

13. The system of claim 12, further comprising a filter element placed at least one of in the inlet or in the outlet of the blower unit that filters the ambient air.

14. The system of claim 12, the at least one heater element being located at least one of (1) within the blower unit, or (2) in the first air flow path between the blower unit and exit opening.

15. The system of claim 14, the processor being further configured to control a temperature of the at least one heater element to produce a selected temperature for the stream of heated air exiting the exit opening of the first air flow path.

16. The system of claim 15, the processor being further programmed to control a flow rate of the return air in the second air flow path to be greater than a flow rate of the stream of air in the first flow path.

17. The system of claim 15, further comprising a data storage unit storing a database of material characteristics for at least one of a plurality of user-selectable target substances or at least one of a plurality of user-selectable surface materials from which the target surface may be formed, the material characteristics including at least one of vaporization temperature ranges for the plurality of target substances, physical property changing temperature ranges for the plurality of target substances, chemical property changing temperature ranges for the plurality of target substances or destructive temperature limits ranges for the plurality of target substances or the plurality of surface materials.

18. The system of claim 17, further comprising a user interface by which a user inputs information regarding at least one of the target substance or the surface material from which the target surface is formed, the processor being further configured to
receive the user input from the user interface,
reference the stored database of material characteristics, and
initially adjust at least one of the flow rate or the temperature of the stream of heated air based on the received user input regarding the at least one of the target substance or the surface material from which the target surface is formed.

19. A system for analyzing a contamination level of a target surface, comprising:
an air analyzer device; and
an inlet device, comprising:
an air supply source;
a first air flow path that directs a stream of air between the air supply source and an exit opening;
at least one heater element that heats the stream of air in the first airflow path upstream of the exit opening, the exit opening being configured to selectively direct the stream of heated air exiting the exit opening toward a target surface, an impingement of the stream of heated air on the target surface causing a release of a target substance by raising a vapor pressure of the target substance, at least a portion of the target substance being entrained in the stream of heated air;
a second air flow path that collects a volume of return air from the target surface, the volume of return air being at least a portion of the stream of heated air with the at least the portion of the target substance entrained therein, the second air flow path being a separate and distinct air flow path from the first air flow path;
a conduit that directs the return air from the second air flow path to an input of the air analyzer for analysis of the target substance entrained in the return air as an indication of a contamination level of the target surface;
a processor that is configured to
control a flow rate of the stream of air by controlling a pressure of air from the air supply source;
receive feedback from the air analyzer regarding a volume of entrained components from the target substance detected in the return air; and
adjust a flow rate and a temperature of the heated stream of air based on the feedback.

* * * * *